United States Patent [19]
Garthe

[11] Patent Number: 5,852,227
[45] Date of Patent: Dec. 22, 1998

[54] APPARATUS FOR MEASURING THE COMPOSITION OF EXHAUST GASES OF INTERNAL COMBUSTION ENGINES

[75] Inventor: Christopher Garthe, Düsseldorf, Germany

[73] Assignee: Pierburg AG, Neuss, Germany

[21] Appl. No.: 863,286

[22] Filed: May 27, 1997

[30] Foreign Application Priority Data

May 25, 1996 [DE] Germany ................ 196 21 293.6

[51] Int. Cl.$^6$ ............................ G01M 15/00; G01N 1/00
[52] U.S. Cl. ......................................................... 73/23.32
[58] Field of Search .......................... 73/23.31, 23.32, 73/118.1, 23.22, 23.35, 23.39, 23.42

[56] References Cited

U.S. PATENT DOCUMENTS 3,558,283  1/1971  Freeman et al. .................. 73/23.31
5,221,517  6/1993  Takeda .............................. 73/23.32

OTHER PUBLICATIONS

Emissions–Und Immissionsmesstechnik Im Verkehrsweesen Tüv–Rheinland Publishers—1993.

Primary Examiner—George M. Dombroske
Attorney, Agent, or Firm—Ladas & Parry

[57] ABSTRACT

Apparatus for the measurement of components of exhaust gas of an internal combustion engine in a flame ionization chamber to which the exhaust gas, combustion gas and combustion air are supplied and in which the gas components in the exhaust gases are measured. The apparatus comprises three connection lines respectively for receiving the exhaust gas, combustion gas and combustion air for supplying these to the flame ionization detector. A separate control line is provided containing a pressure controller and an outlet nozzle body which opens to ambient atmosphere. The control line has a section between the pressure controller and the outlet nozzle body. Each connection line has inlet and outlet flow adjusters defining a respective section therebetween. At least two further lines connect the sections of two of the connection lines to the section of the control line. The inlet and outlet flow adjusters in each of the connection lines are set to provide higher gas flow at the inlet flow adjuster than at the outlet flow adjuster. The outlet flow adjusters are nozzles and the inlet flow adjusters can also be nozzles or pressure controllers.

7 Claims, 2 Drawing Sheets

APPARATUS FOR MEASURING THE COMPOSITION OF EXHAUST GASES OF INTERNAL COMBUSTION ENGINES

FIELD OF THE INVENTION

The invention relates to apparatus for measuring the composition of exhaust gases of internal combustion engines and particularly to such apparatus which employs a flame ionization detector and various supply lines for sample, test and operating gases.

BACKGROUND AND PRIOR ART

Such apparatus is described in the publication Emissions- und Immisionstechnik im Verkherswesen (Emission and Immission Technology under Traffic Conditions), G. Hauschulz, Cologne, TÜV-Rheinland Publishers, 1993, pages 214 and 215. The measurement principle of a flame ionization detector disclosed therein is based on the fact that ions are formed from hydrocarbon molecules in a hydrogen flame. The flame burns between two electrodes, to which a DC voltage is applied. Combustion air and combustion gas are introduced into the burner. The exhaust sample is mixed with the combustion gas in front of the burner nozzle. The ions that form in the flame provide a charge transfer, which can be measured as an ion current. The flame ionization detector disclosed in the publication has various connection lines for supply of sample, test, and operating gases, in each of which lines a precision pressure controller and an outlet nozzle body are arranged, in order to obtain an unvarying flow of the individual components. Therefore, the device will operate precisely, if the pressure drop at the outlet nozzle bodies is accurately maintained, which can be accomplished only by means of expensive pressure controllers which maintain a constant pressure in the lines. Each pressure controller includes a pressure sensor and a valve to provide a precise pressure control in the line and the pressure controller is subject to various manufacturing tolerances. Accordingly, the use of a multiple number of pressure controllers in the system leads to inaccuracy of the measurement results, while also increasing cost.

In the aforesaid publication at page 312, it is disclosed that the hydrocarbon components contained in the exhaust gas comprise a large number of individual components, including methane ($CH_4$), whose contribution to smog formation is relatively small and thus needs to be minimally evaluated.

According to the publication, certain oxidation catalysts can be controlled such that only a minimum amount of $CH_4$ is collected, whereas the other HC compounds are converted to $CO_2$. Thus $CH_4$ and total HC can be determined separately in a flame ionization detector and the methane-free HC emission can be obtained by subtracting the methane from the total HC.

The chemical oxidation of hydrocarbons in the exhaust gases requires the simultaneous presence of the oxygen reaction component in the measurement gas. If the measurement gas is the exhaust gas from automobile engines, then the oxygen content is insufficient. The oxygen required for the conversion to carbon dioxide is introduced into the exhaust gases as so-called combustion air components. The hydrocarbon concentrations occurring in the exhaust gases, however, are too high for conventional converters. Therefore, a dilution of the exhaust gases is necessary, so that the dilution ratio of combustion air to exhaust must be accurately measured in order to be able to determine the total emission. In addition, extra expense is required for further pressure controllers and the like.

SUMMARY OF THE INVENTION

An object of the invention is to provide apparatus for measuring exhaust gas compositions of the above type which are simpler in construction and have a reduced number of parts; particularly pressure controllers, and in which a dilution of the exhaust gases will be obtained that depends on as few parameters as possible.

In order to achieve the above and further objects, the invention is directed to apparatus for the measurement of components of exhaust gas of an internal combustion engine in which sample, test and operating gases are supplied to a flame ionization detector in which the gas components are measured and wherein, according to the invention, three connection lines are provided for respectively receiving sample, test and operating gases for supplying these gases to the flame ionization detector, and a separate control line is provided containing a pressure controller and an outlet nozzle body which opens to the ambient atmosphere. Each of the connection lines has inlet and outlet pressure adjusters therein defining a respective section in said connection line between the inlet and outlet adjusters. At least two further lines connect the sections of two of said connection lines to the control line in a section thereof between the pressure controller and the outlet nozzle body. The inlet and outlet pressure adjusters in each of the connection lines are constituted to provide a higher flow rate at the inlet pressure adjuster than at the outlet pressure adjuster.

The inlet pressure adjuster in each connection line can be constructed as an inlet nozzle body and the outlet adjuster in each connection line as an outlet nozzle body.

In further accordance with the invention, to achieve dilution of the exhaust gas, two branch lines are connected to first and second connection lines and the branch lines are connected to a common line for flow in said common line of a mixture of the gases flowing in said first and second connection lines. A nozzle body is provided in the common line and an inlet nozzle body is provided in each branch line. The common line and the third connection line are connected to form a mixing section for the gases flowing in the common line and in the third connection line. The mixing section extends to the flame ionization chamber and a nozzle body is provided in the mixing section.

The nozzle body in the common line and the outlet pressure adjuster in the third connection line are disposed upstream of a connection point between the common line and the third connection line.

BRIEF DESCRIPTION OF THE FIGURES OF THE DRAWING

Two embodiments of the invention are illustrated in the drawing wherein.

DETAILED DESCRIPTION OF PREFERRED EMBODIMENTS

Figure 1:
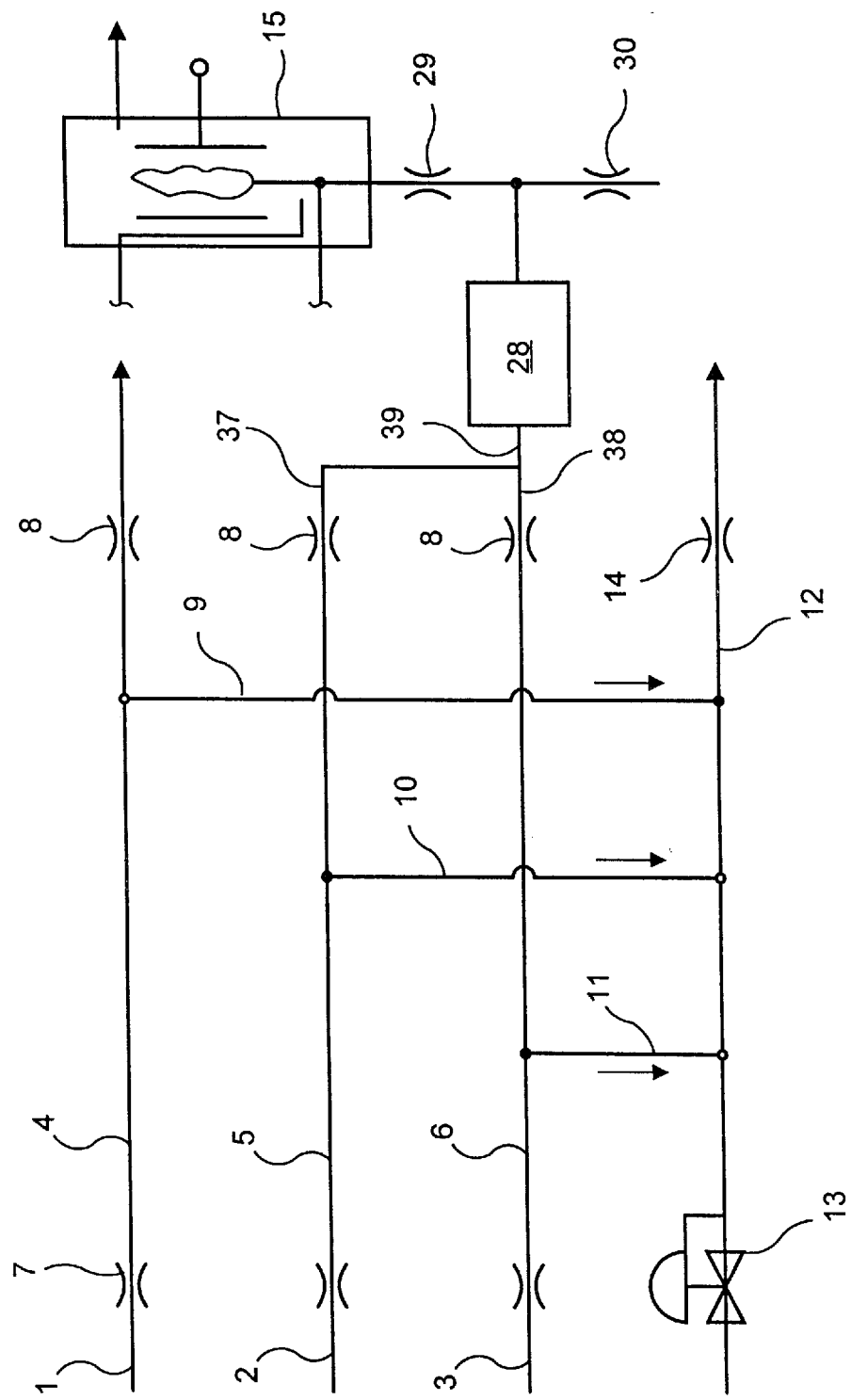
FIG. 1 diagrammatically illustrates a first embodiment showing the principle of operation of apparatus for measuring gases according to the invention.

FIG. 1 shows a device for measuring components in a gas sample and includes connection lines 1, 2, 3 for respectively supplying sample, test and operating gases to a gas analyzer 15 in the form of a flame ionization detector. In the case of measuring exhaust components in the exhaust gas of an internal combustion engine, line 1 supplies combustion air to the analyzer, line 2 supplies combustion gas to the analyzer and line 3 supplies the exhaust gas. The connection lines 1, 2, 3 each has a section 4, 5, 6 located between an inlet nozzle body 7 and an outlet nozzle body 8 provided in each of the connection lines. Sections 4, 5, 6 are respectively connected by connection lines 9, 10, 11 to a section 12 of a control air line. The section 12 is disposed between a pressure controller 13 and an outlet nozzle body 14 connected to the ambient atmosphere. The pressure controller 13 is a conventional pressure control means which self-adjusts and which includes a pressure sensor to sense pressure in the line downstream of a valve which is adjusted by the sensor to maintain constant pressure and flow in the line. The nozzle bodies 7, 8 on the other hand do not self-regulated but provide pressure adjustment and flow control based on velocity of flow through the nozzle throat. The nozzle bodies are constituted so that the flow quantity of the gas at the nozzle bodies 7 is greater than that at nozzle bodies 8 so that a flow quantity through connection lines 9, 10, 11 into control air line 12 takes place. In this way, the pressure controller 13 not only controls the pressure in air line 12 but also the pressure prevailing in the sections 4, 5, 6. Thus, the cost for a multitude of pressure controllers, as previously in common use, is no longer necessary.

The gas components reaching control air line 12 from the individual line sections 4, 5, 6 by means of connection lines 9, 10, 11 is extremely small and exits via nozzle body 14 into the atmosphere. Since the same pressure prevails in all nozzle bodies 8 of connection lines 1, 2, 3, the flow through the nozzle bodies can be precisely regulated. A well-defined ratio of the flow quantities of the particular gases can be formed from all types of gases, if these gases are combined, whereby the exact pressure in nozzle bodies 8 is not critical for the ratio of the components; the nozzle bodies 8 than only insure that variations in the flow quantity, i.e., pressure fluctuations are kept within certain limits. As seen in FIG. 1, outlet sections 37, 38 of lines 2 and 3 are connected to a common section 39 which is connected to a converter 28 in which the gases from the lines are mixed. The mixed gases are supplied to the analyzer 15 via a line having a nozzle body 29 leading to the analyzer and a nozzle body 30 connected to the atmosphere. A precise ratio of the gases in lines 2 and 3 is therefore supplied to the analyzer.

Figure 2:
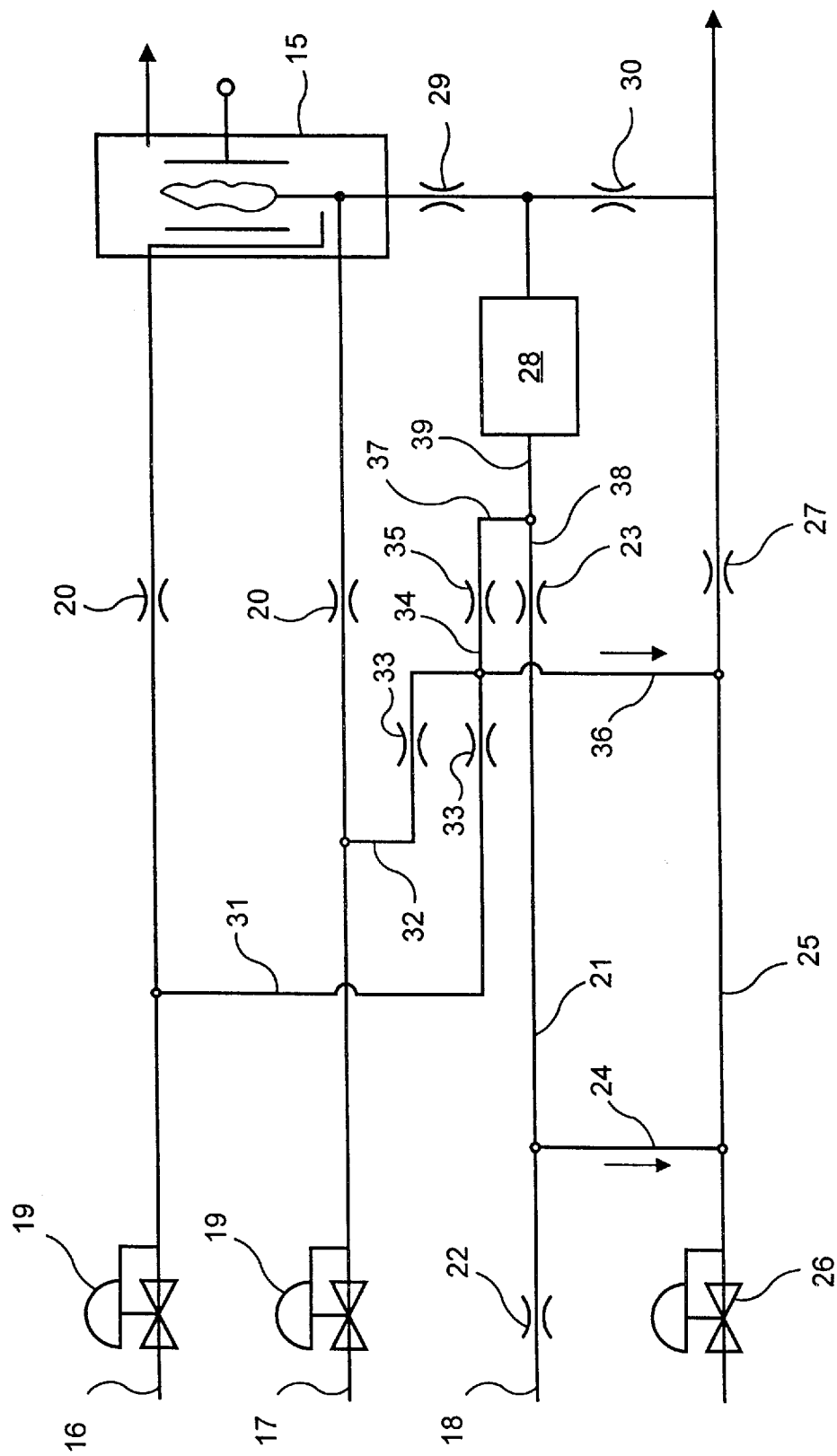
FIG. 2 illustrates a second embodiment adapted specifically for the measurement of HC and $CH_4$ components in exhaust gases.

FIG. 2 shows the flame ionization detector 15 and connection lines 16, 17, 18 respectively for supplying combustion air, combustion gas, and exhaust gases thereto. Lines 16, 17 each include a pressure controller 19 and an outlet nozzle body 20 and the lines are connected to the flame ionization detector 15 to supply combustion air and combustion gas thereto.

Line 18 for supply of exhaust gas has a section 21 between an inlet nozzle body 22 and an outlet nozzle body 23, and section 21 is connected by a connection line 24 to a section 25 of a control air line, said section 25 being defined between a pressure controller 26 and an outlet nozzle body 27 connected to the atmosphere. As in the previous embodiment, the nozzle bodies 22, 23 are constructed so that the flow rate at inlet nozzle body 22 is greater than that at outlet nozzle body 23. Thereby, the flow in line 18 can be regulated by means of connection line 24 into control air line 25.

Exhaust gas line 18 is connected to converter 28 downstream of nozzle body 23, and the exhaust gas line 18 extends from converter 28 to a nozzle body 29 leading to the flame ionization detector 15 and to a bypass nozzle body 30 connected to the control air line 25 downstream of outlet nozzle body 27. Alternatively, nozzle body 30 can open directly into the atmosphere. The combustion air necessary for converting the hydrocarbons, and also, if necessary, for the combustion gas for the flame ionization detector, is introduced into the exhaust gas, i.e., the exhaust gas is diluted to a certain ratio by the combustion air, which itself has been mixed with a small fraction of combustion gas beforehand.

For this purpose, the apparatus has branch lines 31, 32 containing inlet nozzle bodies 33, which branch off from connection lines 16, 17 between pressure controllers 19 and outlet nozzle bodies 20. These branch lines are connected to form a common line section 34 containing an outlet nozzle body 35 downstream from inlet nozzle bodies 33. The inlet nozzle bodies 33 are connected by a connection line 36 to control air line section 25 between pressure controller 26 and nozzle body 27.

Common line section 34 is connected to an exhaust line section 39 existing between outlet nozzle body 23 and converter 28 downstream from outlet nozzle body 35. The same pressure, of course, prevails in sections 37, 38 and 39 at this common outlet point. In order to assure that the ratio of exhaust gas to combustion air remains constant, the pressure must also remain constant in front of outlet nozzle bodies 23, 35. In order to achieve these requirements, the invention provides that outlet nozzle body 35 in common line section 34 and outlet nozzle body 23 in exhaust gas line 21 are subject to the pressure regulated by pressure controller 26 of control air line 25. Thus, the exhaust gas and combustion air are continually mixed in the same ratios at the same pressures prevailing at the input as well as at the output of nozzle bodies 23 and 35. Thus, it does not matter if the pressure varies at the output of outlet nozzle bodies 23, 35. Even if the controlled pressure at the inputs of the outlet nozzle bodies varies, for example, if pressure controller 26 does not operate precisely, this does not change the mixing ratio. Thus, a well-defined ratio of the flow quantities can be obtained of the exhaust gas and combustion air, which must be constant and reproducible for determining the exhaust gas concentration.

In the simplest design, at least two line sections 37, 38 disposed downstream from outlet nozzle bodies 8 (FIG. 1) or 23, 35 (FIG. 2) open into a common line section 39 in which a mixture is produced of the gases that arrive thereat.

Although the invention has been described in relation to specific embodiments thereof, it will become apparent to those skilled in the art that numerous modifications and variations can be made within the scope and spirit of the invention as defined by the attached claims.

What is claimed is:

1. Apparatus for the measurement of components of exhaust gas of an internal combustion engine in which sample, test and operating gases are supplied to a flame ionization detector in which the gas components are measured, said apparatus comprising:

three connection lines respectively for receiving sample, test and operating gases for supplying the gases to the flame ionization detector, a control line, a pressure controller in said control line and an outlet nozzle in said control line which opens into ambient atmosphere, said control line having a section between said pressure controller and said outlet nozzle, each of said connection lines having inlet and outlet pressure regulator means therein defining respective sections in said connection lines between the inlet and outlet regulator means, and at least two further lines connecting the sections of two of said connection lines to said section of said control line, said inlet and outlet pressure regulator means in each of said connection lines being set to provide higher gas flow at the inlet pressure regulator means than at the outlet pressure regulator means.

2. Apparatus as claimed in claim 1, wherein said inlet pressure regulator means in each connection line comprises an inlet nozzle body and said outlet pressure regulator means in each connection line comprises an outlet nozzle body, said pressure controller in said control line adjusting the flow in said control line to provide a constant pressure in said control line.

3. Apparatus as claimed in claim 1, comprising branch lines connected to first and second connection lines, a common line connected to said branch lines for flow in said common line to the flame ionization detector of a mixture of the gases in said first and second connection lines, a nozzle body in said common line and an inlet nozzle body in each branch line.

4. Apparatus as claimed in claim 3, wherein said common line and the third connection line are connected to form a mixing section for the gases flowing therein which mixing section extends to said flame ionization detector.

5. Apparatus as claimed in claim 4, comprising a further nozzle body in said mixing section upstream from said detector.

6. Apparatus as claimed in claim 5, wherein the nozzle body in said common line and said outlet pressure regulator means in said third connection line are disposed upstream of a connection between said common line and said third connection line and downstream from a connection of said common line and said third line to said air control line.

7. Apparatus as claimed in claim 1, wherein said sample, test and operating gases respectively comprise exhaust gas, combustion air and combustion gas.

\* \* \* \* \*